(12) United States Patent
Aronson (10) Patent No.: US 8,910,643 B2
(45) Date of Patent: Dec. 16, 2014

(54) ULTRASONIC MANIPULATOR OF DENTAL FLOSS AND METHOD FOR OPERATING THE SAME

(76) Inventor: Ross E. Aronson, Rye Brook, NY (US)

( * ) Notice: Subject to any disclaimer, the term of this patent is extended or adjusted under 35 U.S.C. 154(b) by 170 days.

(21) Appl. No.: 13/452,601

(22) Filed: Apr. 20, 2012

(65) Prior Publication Data

US 2012/0266904 A1    Oct. 25, 2012

Related U.S. Application Data

(60) Provisional application No. 61/517,432, filed on Apr. 20, 2011.

(51) Int. Cl.
*A61C 17/16*    (2006.01)
*A61C 15/04*    (2006.01)

(52) U.S. Cl.
CPC ............. *A61C 15/047* (2013.01); *A61C 15/043* (2013.01)
USPC ..... 132/322; 132/325; 242/413.3; 242/418.1; 242/420.6

(58) Field of Classification Search
CPC ............................. A61C 15/047; A61C 17/20
USPC ............... 132/322–327; 15/22.1, 167.1, 22.2; 242/418, 418.1, 419, 419.1, 420, 242/420.5, 420.6, 413, 413.3
See application file for complete search history.

(56) References Cited

U.S. PATENT DOCUMENTS

| | | | | |
|---|---|---|---|---|
| 3,847,167 A | * | 11/1974 | Brien ............................. | 132/322 |
| 4,245,658 A | * | 1/1981 | Lecouturier .................. | 132/322 |
| 4,265,257 A | * | 5/1981 | Salyer ........................... | 132/322 |
| 4,307,740 A | * | 12/1981 | Florindez et al. ............. | 132/322 |
| 4,341,363 A | * | 7/1982 | Inatome ...................... | 242/334.1 |
| 4,458,702 A | * | 7/1984 | Grollimund .................. | 132/322 |
| 4,513,229 A | * | 4/1985 | Kudelski ........................... | 318/7 |
| 4,586,521 A | * | 5/1986 | Urso ............................. | 132/322 |
| 4,605,025 A | * | 8/1986 | McSpadden .................. | 132/322 |
| 5,016,660 A | * | 5/1991 | Boggs ........................... | 132/322 |
| 5,170,809 A | * | 12/1992 | Imai et al. ..................... | 132/322 |
| 5,269,331 A | * | 12/1993 | Tanriverdi .................... | 132/325 |
| 5,311,632 A | * | 5/1994 | Center .......................... | 15/22.1 |
| 5,323,796 A | * | 6/1994 | Urso ............................. | 132/322 |
| 5,343,883 A | * | 9/1994 | Murayama .................... | 132/322 |
| 5,639,040 A | * | 6/1997 | Honjo ........................... | 242/334 |
| 5,678,578 A | * | 10/1997 | Kossak et al. ................. | 132/322 |
| 5,762,078 A | * | 6/1998 | Zebuhr .......................... | 132/322 |
| 5,769,102 A | * | 6/1998 | Zebuhr .......................... | 132/322 |
| 5,816,271 A | * | 10/1998 | Urso ............................. | 132/322 |
| 5,860,435 A | * | 1/1999 | Hippensteel .................. | 132/325 |
| 7,055,531 B2 | * | 6/2006 | Rehkemper ................... | 132/322 |
| 7,082,950 B2 | * | 8/2006 | Kossak et al. ................. | 132/325 |
| 7,156,108 B2 | * | 1/2007 | Xin ............................... | 132/322 |

(Continued)

FOREIGN PATENT DOCUMENTS

WO    WO 2005023144    *  5/2005    ............. A61C 17/22

*Primary Examiner* — Robyn Doan
*Assistant Examiner* — Tatiana Nobrega
(74) *Attorney, Agent, or Firm* — Myron Greenspan; Lackenbach Siegel (57) ABSTRACT

An ultrasonic manipulator of dental floss is provided with an ultrasonic mechanism and a floss creep controller mechanism to enable periodic floss creep during use and a reverse of creep upon a tension designation. A process controller controls floss driving and an eccentric mechanism, and a user pause function allows a stop of floss motion and a locking of drive motors to allow floss to resist undue stress and to minimize damage to drive mechanism.

17 Claims, 5 Drawing Sheets

(56) References Cited

U.S. PATENT DOCUMENTS

| | | | |
|---|---|---|---|
| 8,398,399 B2* | 3/2013 | Paschke | 433/119 |
| 2002/0106607 A1* | 8/2002 | Horowitz | 433/118 |
| 2005/0076933 A1* | 4/2005 | Getgey et al. | 132/322 |
| 2010/0139689 A1* | 6/2010 | Couch | 132/322 |
| 2010/0206324 A1* | 8/2010 | Paschke | 132/322 |
| 2012/0234349 A1* | 9/2012 | Pruett | 132/322 |

* cited by examiner

ULTRASONIC MANIPULATOR OF DENTAL FLOSS AND METHOD FOR OPERATING THE SAME

CROSS REFERENCE TO RELATED APPLICATIONS

This application relates to and claims priority from U.S. Ser. No. 61/517,432 filed Apr. 20, 2011, the entire contents of which are incorporated herein by reference.

FIGURE SELECTED FOR PUBLICATION

FIG. 1

BACKGROUND OF THE INVENTION

1. Field of the Invention

The present invention relates to an economical ultrasonic manipulator of dental floss and an automated flossing device. More particularly, this invention relates to an economical hand tool and method of using the same that enables creep conservation of dental floss, ultrasonic vibratory motion, and a process control to manage a creep selection during a use thereof.

2. Description of the Related Art

Gum disease is a health hazard indiscriminately affecting the young and the old. Aside from serious surgical procedures, proper dental hygiene may help minimize and even prevent the effects of the disease by removal of plaque. Consumer organizations report that the most important aspect of the dental hygiene is flossing.

Proper flossing by hand, however, is an arduous and requires great skill and dexterity to properly manipulate the floss in an effort to clean all the interdental surfaces down to the attached gingiva. An automated manipulator of dental floss reduces the amount of tedious work, perseverance, and dexterity required for proper flossing. Unfortunately, simply employing a physical holder for the floss is also insufficient to improve cleaning and necessarily greatly enhance the cost of any such item.

High cost and complex battery-powered floss manipulators are disclosed, among others, in U.S. Pat. No. 5,323,796 (Urso) and U.S. Pat. No. 4,880,382 (Moret et al.), the full contents of each of which are incorporated herein by reference. In particular, each of the disclosed floss manipulators includes several mechanical units all structurally and functionally coupled to one another. One of the units is operative to displace a floss between teeth with lateral strokes guiding the floss along a floss transition path through the tight spot where adjacent teeth come in contact. Another unit is configured to reciprocate the floss in a plane which extends transversely to this transition path. Still another unit is operative to protect the teeth and gums from being hammered by moving parts that reciprocate the floss span. And yet another unit is adapted to and requires a continuously replacement of the floss span.

The units have respective drives, and in some cases multiple drives, each including a multiplicity of gear trains which selectively intermesh with one another to drive the desired unit upon actuating an input shaft continuously throughout operation (e.g., without stoppage). Gear manufacturing, particularly when relatively small-size gears are required, is a time consuming and labor intensive process driving up manufacturing costs. The maintenance of the disclosed manipulator may also be problematic due to numerous mechanical components that are not easy to replace if the situation requires such a replacement.

Necessarily, each of these devices requires a complex geometry, maintenance, and due to their complexity also frequently brake down (difficult to re-spool, retention, internal and external drive members snap etc.) Further, such devices are often broken due to over-force upon insertion between closely aligned teeth (tight fit) which over-stresses any feeding mechanism and associated gearing. Accordingly, a need therefore exists for an automated ultrasonic floss manipulator having a simple, but reliable structure and which is economical during use.

Also accordingly, there is a need for an improved method of using an economical device with manual control of any floss creep which minimizes damage thereof in an operative condition.

ASPECTS AND SUMMARY OF THE INVENTION

In response, it is now recognized that there is a need for an economic ultrasonic manipulator of dental floss that is operative to eliminate drive damage in an over-stress condition while maintaining a conservative floss-creep process control.

In one alternative aspect of the proposed invention an ultrasonic manipulator of dental floss is provided with an ultrasonic mechanism and a floss creep controller mechanism to enable periodic floss creep during use and a reverse of creep upon a tension designation. A process controller controls floss driving and an eccentric mechanism, and a user pause function allows a stop of floss motion and a locking of drive motors to allow floss to resist undue stress and to minimize damage to drive mechanism.

In another alternative aspect of the proposed invention an automated floss dispenser is configured with a housing and a lever which is pivotally mounted to the housing and has a fork-shaped free end. The housing encloses a floss-dispensing and lever-actuating drives. The floss-dispensing drive includes spaced floss-dispensing and floss take up reels reciprocally rotatable about parallel reel axes so as to provide a desired tension to a floss guided along a path extending between the dispensing and take-up reels through the fork-shaped end of the lever. The automated floss dispenser further has a controller operative to control the floss dispensing drive so that the reels temporarily change the rotational direction thereof if the tension force applied to the floss does not correspond to a reference value.

According to one alternative embodiment of the present invention, there is proposed a method for operating an ultrasonic manipulator of dental floss, said method comprising the steps of: initiating a process controller function for operative interaction of a computerized process controller; monitoring a tension of said dental floss operatively coupled between a dispensing reel and a take-up reel; verifying said tension is within a predetermined desired tension range; operating a creep motor drive in a first direction to dispense said dental floss along a floss path in said first direction; operating an eccentric system operatively coupled with said ultra sonic manipulator to provide an ultrasonic manipulation of said dental floss during a use thereof; and operating said computerized process controller to conduct at least the following steps: (a) a creeping said dental floss in said first direction; (b) a monitoring said tension; and (c) an operating said creep motor drive in a second direction opposite to said first direction to retract said dental floss along said floss path in said second direction when said tension exceeds said predetermined desired tension range.

According to another alternative embodiment of the present invention, there is provided a method, further comprising the steps of: stopping said creep drive motor and locking said creep drive motor upon the initiation of a creep pause function in said method; and releasing said locking of said creep drive motor and operating said creep drive motor upon a termination of said creep pause function, whereby said method allows for a temporary termination of creep during said use.

According to another alternative embodiment of the present invention, there is provided an automated floss dispenser system, comprising: a housing extending along a longitudinal axis; an eccentric mechanism operative to provide an ultrasonic energy to a portion of said housing proximate a fork-shaped distal end; a floss-dispensing drive operative to advance a floss and including respective dispensing and take-up reels mounted in the housing, the floss advancing along a path extending between the reels through spaced ends of the fork-shaped distal end; and a controller controlling the dispensing drive so that the reels are reciprocally rotated about respective parallel reel axes, which extend transversely to the longitudinal axis, to net transfer the floss from the dispensing reel to the take-up reel during a use thereof.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' or 'operates' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 1:
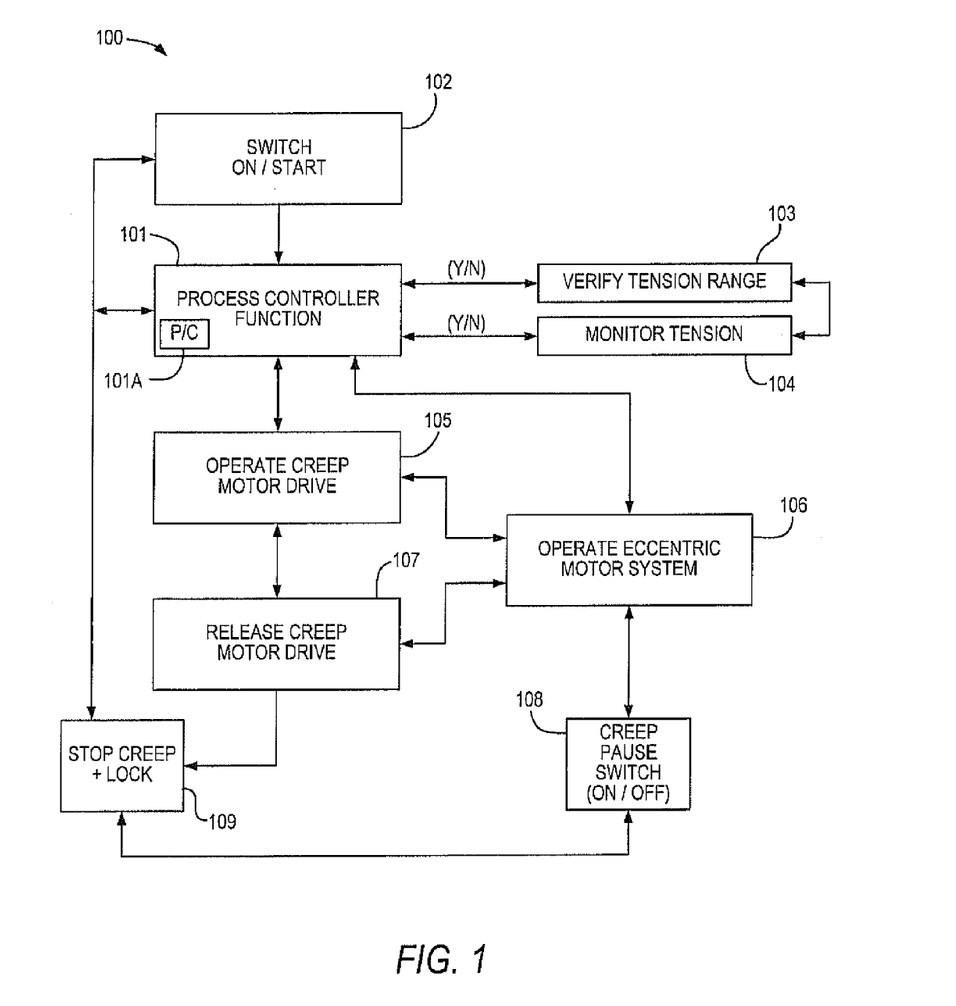
FIG. 1 is an illustrative flow chart of one aspect the proposed invention and method for operating an economic ultrasonic manipulator of dental floss.

Referring now to FIG. 1, operable methods of using the proposed economic ultrasonic manipulator of dental floss are provided in method 100. It shall be understood by those of skill in the art that method 100 may include all, or a portion of the following discussed particular method steps without departing from the scope and spirit of the present invention.

In a first step a control switch 102, in operative control of process elements as discussed in this application, is actuated to an on position and a pin a second step a processor control function 101 is triggered including operative interaction with an included process control chip or device 101A. Thereafter, a verify tension range step 103 for a tension detector device (discussed later) is actuated as is an ongoing monitor tension step 104. It will be understood that the tension verification and monitoring steps may be simultaneous with each other and with other steps and features in proposed method 100 without deviating from the scope of the proposed invention. Operatively interlinked with process control function 101 are steps of operation of a creep motor 105 and an operation of an eccentric motor system 106 to generate an ultrasonic vibration of dental floss (as will be later discussed). During one aspect of use, where an empty/full floss-spool tension is determined by steps 103, 104 a step of reversing creep drive motor 107 is conducted so that the floss is transited in a reverse direction in a creep process.

Regarding the creep motion, it will be understood by those of skill in the art that the transfer motion is small, on the order of several millimeters to several centimeters per minute between spools. It will also be understood that this rate may be varied widely by either direct user control of or by an automatic step of process control 101A in the process controller function step 101, without departing from the scope and spirit of the present invention. As a result, it will be understood that slow forward creep of the floss will occur until either verify tension range step 103 or monitor tension step 104 trigger an over-tension signal to process control function 101—and thereupon cease to operate creep motor 105, or upon actuation of a user-control creep pause switch step 108. Creep pause switch step 108 is in operative cooperation with a stop creep and lock step 109.

In stop creep and lock step 109 it will be understood that this step may be triggered by manual creep switch step 108, or an interaction with process controller function 101. For example, a step 108 where a manual creep pause is actuated, a user may wish to force dental floss between closely positioned teeth and need to apply greater manual pressure—and wish to temporary 'lock' the dental floss to prevent slacking and de-spoiling or may otherwise exceed the tension range permitted by monitor tension step 104. In this way, method 100 enables either automatic stop creep lock (via process controller function 101) or a manual selection via creep pause switch step 108. And, correspondingly an improved function and improved economy preventing waste of dental floss.

As a further improvement provided by method 100, it will be understood that reverse creep motor drive step 107 will allow re-use of previously-spooled floss from a (later discussed) floss dispensing mechanism. For example, where the floss remains in good usable condition.

Overall, it will be understood that FIG. 1, and method 100, illustrates a number of method steps and optional and interoperative steps allowing for the convenient use of the economical ultrasonic device as proposed.

Figure 2:
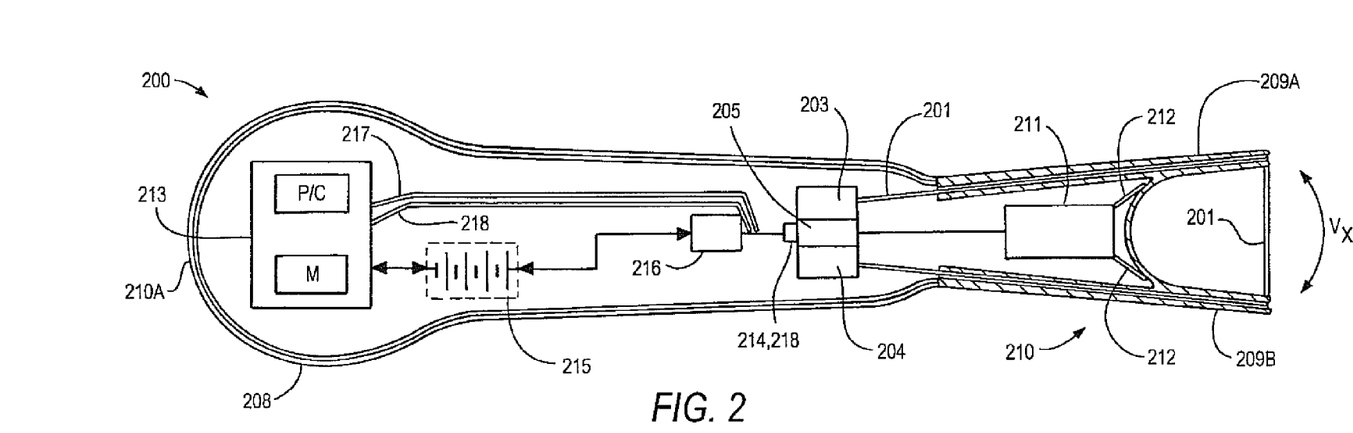
FIG. 2 is an illustrative open-body view of one embodiment of the proposed invention for an ultrasonic manipulator of dental floss.
Figure 3:
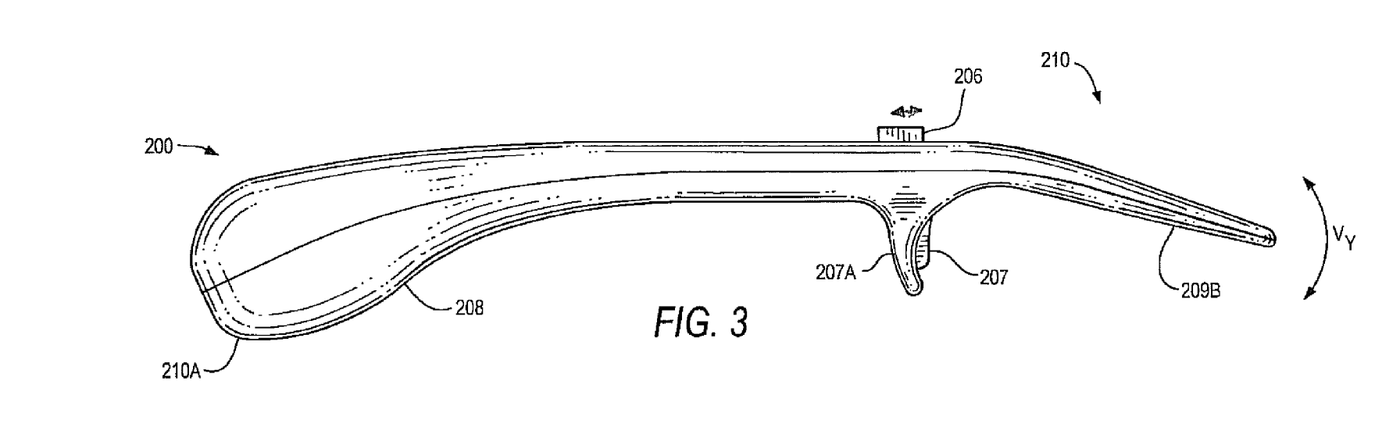
FIG. 3 is an illustrative side view of FIG. 2.

Referring now to FIGS. 2 and 3 an ultrasonic floss dispenser system 200 is proposed wherein floss 201 is retained and spooled along a floss route and pathway or groove series 202 between a dispensing-reel 203 and a take-up reel 204 operatively engaged with a drive motor and spool lock system 205 enabling rotation, driving, and locking of respective dispensing-reel 203 and take-up reel 204 in reverse direction. For example, during operation (discussed earlier) of a creep pause, drive motor and spool lock system 205 stops creep driving (from a drive motor 216) and locks both spools 203, 204 such that a movement of floss 201 along floss route 202 temporarily ceases.

A control switch mechanism 206 is in operative control with drive motor and drive lock mechanism 205 and allows for on/off operation and is operatively interlinked with a process controller system 213 containing a process controller (P/C) and associated memory (M) and circuitry for receiving on/off signals from control switch 206 and from other sensors in floss dispenser system 200, as will be discussed. Process controller system 213 is a central processing unit configured as an article of manufacture which is capable of reading a loaded software.

Process controller system 213 is in operative communication with a power source 215 for operative driving drive motor 216 and drive motor and spool lock 205. In operative association with said dispensing-reel and take-up reel 203, 204 is a tension monitor sensor 214 operative to relay a tension measurement via a tension sensor coupler path 217 to process controller 213 for system operation. As a back-up safety mechanism a drive motor and drive lock sensor 218 proximate said tension monitor sensor 218 transmits a drive motor status and drive lock status along a sensor information path 218 to process controller 213. Similarly, a creep pause lock switch mechanism 207 is operative proximate a trigger region 207A on a handle body housing 208. Creep pause lock switch mechanism 207 is in operative communication with process controller 213 and allows for temporary creep pause and locking of said drive motor during a use upon a user initiation.

Projecting from handle body housing 208 are a pair of arms 209A and 209B extending along a distal end portion 210 opposite a handle portion 210A. Secured proximate distal end portion 210 is an eccentric motor mechanism 211 (miniaturized) receiving a drive power from said power source 215 and in an operative control connection with said process controller 213. Eccentric motor mechanism 211 is small, and is secured in handle housing body 208. As a result, process controller 213 is in operative control of eccentric motor mechanism 211 and transfers vibration energy thereto. To emphasize this vibration, one or more mechanical eccentric motion couplers 212, 212 (two are shown) allow transfer of ultrasonic motion directly from eccentric motor mechanism 211 via couplers 212, 212 to extending projecting arm prongs 209, 209, thereby avoiding vibratory energy loss over a long distance of travel from vibration-source-to-floss, and undue mechanical complexity, as is present in the related art.

During use, it will be understood that eccentric motor 211 provides motion on at least one, and preferably two axes (x-axis and y-axis), such that there is an ultrasonic vibration movement of prongs 209, 209 in directions $V_x$ and $V_y$, as shown in FIGS. 2 and 3. Similarly during use, floss 201 will be understood to creep in one direction between prongs 209, 209 in a first direction (except when creep is paused as discussed earlier) until a tension noting an empty spool is reached and reverse creep drive motion is begun in a second direction. Although not preferred, it will be understood as within the scope of the invention that a reverse-creep trigger process could be operative in process controller 213 to occur upon each release of creep pause lock switch 207, or upon a tension that is less than a maximum tension range trigger such that floss 201 is reversed in motion at a frequency that is greater than between the ends of each spool. In this way, those of skill in the art will recognize that a floss dispensing system 200 can be operated with a limited length of floss (less than full spools) so to enable a reduced dimension.

Figure 4:
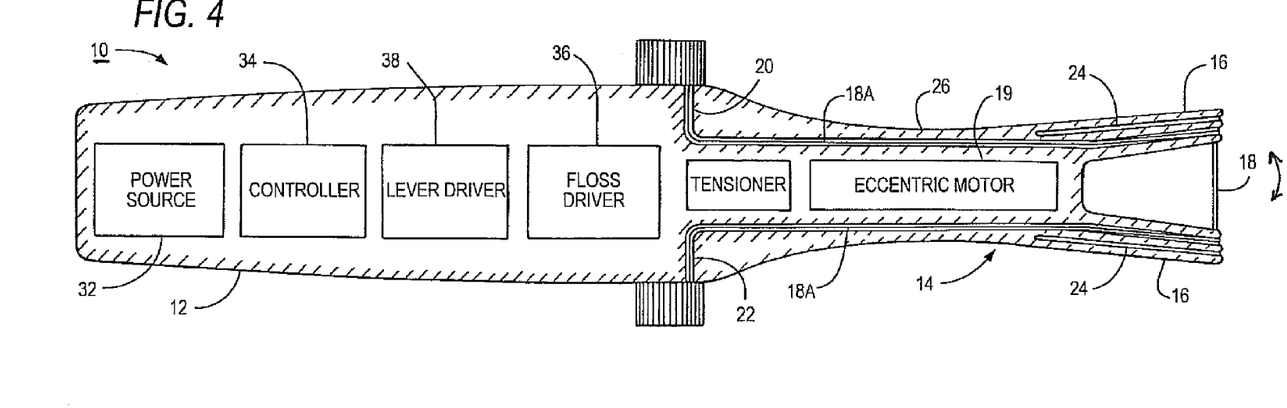
FIG. 4 is an illustrative top view of an alternative embodiment of the proposed invention for a manipulator of dental floss.
Figure 5:
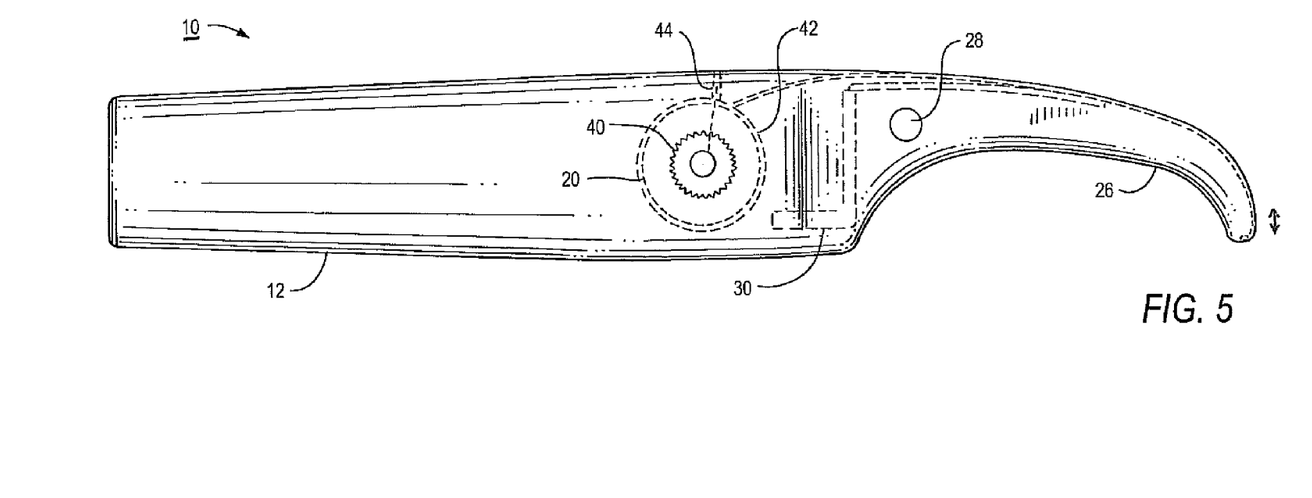
FIG. 5 is an illustrative side view of FIG. 4.

Referring alternatively now to FIGS. 4 and 5, an alternative and optional embodiment of the proposed invention is provided. As shown, a floss dispenser 10 is configured to route floss 18 along a floss route 18A, from a dispensing spool 20, through guide grooves 18A (respectively) and to a take-up reel 22. The floss 18 is wound in a groove 42 (FIG. 5) of reel 20, respectively, and further guided along slots 18A (FIG. 4) configured in a housing 12 having an extended portion 14. Thus, during a use floss 18 unwound from grove 42 dispensing spool 20 runs along slots 18A, spans across a U-shaped distal end 24 and further travels along grove 18 before being attached to the groove of take-up spool 22, which is configured identically with groove 42 of dispensing spool 20.

The dispenser 10 is configured with a hollow housing 12 for receiving components, and may have different cross-sections tapering towards the proximal end of dispenser 10. The extended portion 14 extends outwards from the distal end 12 of housing 12 and has a pair of protecting prongs 16, 16 (as shown) which define the fork-shaped distal end of dispenser 10.

Positioned laterally inwards from protective prongs 16, 16 is a pair of reciprocating tines 24, 24 which define a distal portion of a lever 26 pivotally mounted to cantilever 16 by a pin 28 (FIG. 5). A proximal end 30 of lever 26 is illustrated as being received in the open distal end of housing 12 so as to move up and down while the lever pivots about pin 28.

The housing 12 further encloses a power source 32 including, for example, a battery that can be turned on/off by a knob (not shown) located on housing 12. A floss drive 36 actuating a floss-dispensing mechanism is also mounted in housing 12 and operatively connected to dispensing reel 20 and take-up reel 22. A lever drive 38 located in housing 12 is extending and operative to actuate lever 26 to transfer ultrasonic vibration to prongs 16, 16.

The operation of dispenser 10 is fully automated and controlled by a central processing unit 34 configured as an article of manufacture which is capable of reading a loaded software. In response to the actuation of battery 32, control signals are generated by controller 34 and coupled in respective lever and floss drives 36 and 38, respectively. The floss drive 36 provides the translation of floss 18 between reels 20 and 22, respectively, while lever 26 with tines 24 are actuated by lever drive 38 so as to reciprocate in a plane extending transversely to the plane in which the floss is translated.

The floss drive 36 includes, for example, a DC step motor having a motor shaft 44 which is coupled to shafts 40 of respective reels 20 and 22. The shaft 44, which is controlled as disclosed hereinbelow, is operative to periodically change its rotation between clockwise and counterclockwise directions so as to provide a reciprocal creep motion of floss 18 upon the conditions set forth above (e.g., tension max or a creep pause instruction). The drive 36 operates so that the reels rotate more in a take-up or unwinding direction than in the opposite direction to net-transfer floss 18 from dispensing reel 20 to take-up reel 22. The sequence of another alternative drive operation method is controlled by controller 34 as explained immediately below.

Figure 6:
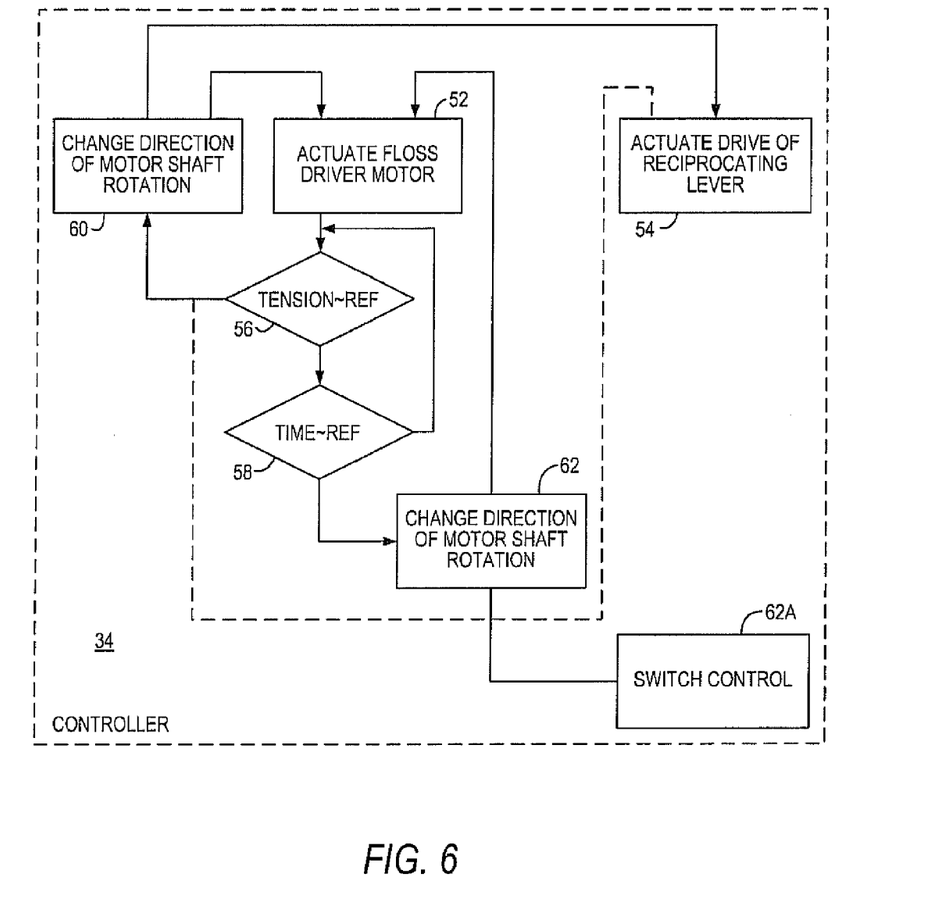
FIG. 6 is a flow chart illustrating one alternative operation of the floss-dispensing and floss-taking-up mechanisms of the disclosed manipulator in accordance with one embodiment of the invention.

FIG. 6, discussed in light of FIGS. 4 and 5, illustrates one of the aspects of the disclosed configuration which has single floss drive 36 (FIG. 4) actuating the shafts of respective reels 20 and 22, as shown in step 52. Simultaneously with step 52, lever drive 38 actuates a mechanism operative to pivot lever 26 about pin 28 relative to housing 12 as illustrated by step 54.

As floss 18 penetrates an inter-teeth space and is moved in opposite directions, it may hit a tight spot slowing the floss travel speed which, in turn, is manifested by slack and/or tension sensed by a speed or tension-force detector 18 of FIG. 4, as shown in step 56. The sensor 18 continuously generates a signal processed in controller 34. Once the processed signal substantially differs from a corresponding stored reference value, the rotation of shaft 44 (FIG. 5.) is optionally either temporarily locked and then released or is optionally reversed, as shown in step 60. Upon restoring the desired tension, the shaft's rotation is again continued according to process control parameters.

When the formation of the slack is sensed, controller 34 generates a control signal coupled into and switching off lever drive 38 which interrupts the reciprocating motion of lever 26. The lever drive 38 is actuated again in response to the corresponding control signal from controller 34 upon restoring the desired tension of floss 18.

The time period during which shaft 44 of floss drive 38 rotates in the unwinding direction is greater than that one in the opposite direction and monitored in step 58. The shaft 44 continues to rotate in the original direction until the monitored time corresponds to a stored reference value. Thereafter, controller 34 generates another control signal having shaft 44 change its direction, cease a creep motion, or otherwise as can be programmed and as illustrated in step 62. As will be understood, a switch control option 62A may also allow for user-selection of change in shaft rotation or shaft lock. Obviously, the time-related reference values for respective rotational directions differ from one another. The controller 34 is provided with a software capable of reading only actual time during which the floss advances in each of the opposite directions. In other words, the time necessary for restoring the desired tension is not factored in the decision made by controller 34 with respect to the actual time of rotation of shaft 44 in step 58.

Figure 7:
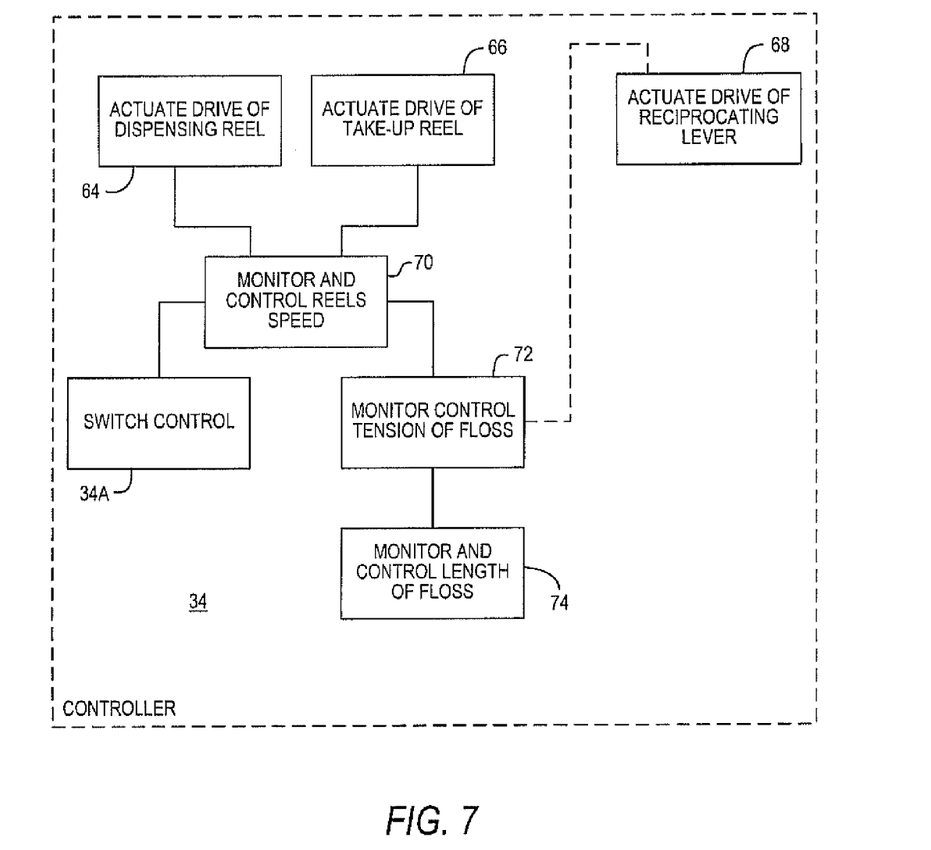
FIG. 7 is a flow chart illustrating operation of the manipulator of FIG. 4 in accordance with a further embodiment of the floss-dispensing and floss-receiving mechanisms.

FIG. 7, discussed in conjunction with FIGS. 4 and 5, illustrates a further aspect of the disclosed configuration which, in contrast to the configuration of FIG. 6, includes two separate floss drives in operative communication with a switch control 34A in operative communication with controller 34. In use, therefore, both floss drives, which include respective stepmotors operative to reverse the rotational direction, are simultaneously actuated at steps 64 and 66. To ensure that the rotational speed in the unwinding direction is greater than the speed in the opposite direction, there is no need to control separately the speeds of respective reels 20 and 22. It is sufficient to control the desired speed difference between the shafts rotating respective reels 20 and 22, as shown in step 70. Of course, the algorithm supporting the desired speed difference may include differentiating, integrating and other known measuring techniques. The control of the desired tension of the floss is implemented in step 72 analogously to the tension control step of FIG. 6 and controls the change of rotational direction and periodic interruption of the reciprocal displacement of lever 26, as indicated by step 68. The controller 34 is also provided with a software capable of controlling the total length of floss 18 and timely preventing the actuation of the floss drives of FIG. 4 or drive of FIG. 6 if the total unwound length corresponds to a reference value, as shown in step 74.

Having described at least one of the preferred embodiments of the present invention with reference to the accompanying drawings, it will be apparent to those skills that the invention is not limited to those precise embodiments, and thus, it is intended that the present disclosure cover modifications and variations of this disclosure provided they come within the scope of the appended claims and their equivalents.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. 112, paragraph 6 to define the invention. To the contrary, if the provisions of 35 U.S.C. 112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. 112, paragraph 6. Moreover, even if the provisions of 35 U.S.C. 112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function. Therefore, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

What is claimed is:

1. An automated floss dispenser system, comprising:
 a housing extending along a longitudinal axis and having a proximal handle portion at one axial end of said housing and a distal portion including a fork-shaped end comprising two projecting arms having free distal ends;
 dispensing and take-up reels mounted within said housing; floss extends from said dispensing reel across said free distal ends of said projecting arms to said take-up reel where an operative portion of said floss is the portion of floss between said free distal ends of said projecting arms;

an eccentric motor within said distal portion of said housing, said eccentric motor provides ultrasonic energy to said fork-shaped distal end and said operative portion of floss;

a floss-dispensing drive system comprising a drive motor provided in said housing and being operative to reciprocally rotate said dispensing and take-up reels to net transfer said floss from said dispensing reel to said take-up reel;

a controller including a process control chip and memory programmed to control the floss-dispensing drive;

a tension sensor operatively coupled to the controller where said tension sensor continuously senses the tension in said floss during displacement thereof and generates a signal to the controller indicating the detected tension; wherein the controller compares the detected tension to a stored reference value or range and if the detected tension value does not correspond with said stored reference value or range, the controller generates a control signal to either stop rotation of the reels or change the rotational direction of said reels until the detected tension is restored to said stored reference value or range;

a creep pause lock switch provided on said proximal handle portion of said housing; said creep pause lock switch being in operative communication with said controller and temporarily locks said drive motor and pauses creeping of said floss when actuated;

wherein said controller is provided with software that monitors the actual time the floss advances so that when a total unwound length of floss corresponds to a reference value, the controller provides a signal to said floss-dispensing drive system to cease rotation of said reels, where time necessary for restoring tension to said stored reference value or range is not included in said actual time monitored by said software.

2. An automated floss dispenser system as defined in claim 1, wherein said reels are reciprocally rotated about respective parallel reel axes, which extend transversely to the longitudinal axis.

3. An automated floss dispenser system as defined in claim 1, wherein one or more mechanical eccentric motion couplers are coupled to said projecting arms to transfer ultrasonic energy directly from said eccentric motor to said projecting arms.

4. An automated floss dispenser system as defined in claim 1, wherein said eccentric motor is mounted to provide motion along at least one direction or axis substantially normal to said housing longitudinal axis.

5. An automated floss dispenser system as defined in claim 4, wherein said motion of said free distal ends includes movements along two axes.

6. An automated floss dispenser system as defined in claim 5, wherein said two axes are substantially normal to said longitudinal axis and to each other.

7. An automated floss dispenser system as defined in claim 1, wherein a pair of reciprocating tines is positioned laterally inwards from said projecting arms, said pair of tines define a distal portion of a lever.

8. An automated floss dispenser system as defined in claim 7, wherein said lever has a proximal portion opposite said distal portion defining said pair of reciprocating tines and said lever is pivotally mounted to said distal portion of said housing at a pivot provided between said distal portion of the lever and said proximal portion of the lever, wherein said proximal portion of said lever moves up and down within said housing while said lever and projecting arms pivot.

9. An automated floss dispenser system as defined in claim 8, wherein a pin pivotally mounts said lever and said projecting arms.

10. An automated floss dispenser system as defined in claim 1, wherein said drive motor comprises a step motor.

11. An automated floss dispenser system as defined in claim 1, wherein said controller is programmed to control a desired speed difference between the dispensing and take up reels.

12. An automated floss dispenser system as defined in claim 11, wherein said controller is programmed to use a differentiating measuring technique.

13. An automated floss dispenser system as defined in claim 11, wherein said controller is programmed to use an integrating measuring technique.

14. An automated floss dispenser system as defined in claim 1, wherein two separate floss drives are provided in operative communication with said controller.

15. An automated floss dispenser system as defined in claim 14, wherein said two separate floss drives each comprises a step motor.

16. An automated floss dispenser system as defined in claim 11, further comprising a switch control in operative communication with said floss drives and said controller.

17. An automated floss dispenser system as defined in claim 10, wherein said step motor comprises a DC step motor.

* * * * *